United States Patent
Fujikura

(10) Patent No.: US 7,586,615 B2
(45) Date of Patent: Sep. 8, 2009

(54) MEASURING UNIT

(75) Inventor: Tatsuo Fujikura, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 241 days.

(21) Appl. No.: 11/211,602

(22) Filed: Aug. 26, 2005

(65) Prior Publication Data

US 2006/0044563 A1   Mar. 2, 2006

(30) Foreign Application Priority Data

Aug. 26, 2004 (JP) ............................. 2004-246879

(51) Int. Cl.
G01N 21/55 (2006.01)
(52) U.S. Cl. ...................................... 356/445
(58) Field of Classification Search ........................ None
See application file for complete search history.

(56) References Cited

U.S. PATENT DOCUMENTS

| | | | |
|---|---|---|---|
| 4,602,869 A * | 7/1986 | Harrick | ........................ 356/244 |
| 5,362,445 A | 11/1994 | Miyahara et al. | |
| 6,143,250 A | 11/2000 | Tajima | |
| 7,358,079 B2 | 4/2008 | Schurmann-Mader et al. | |
| 2001/0040130 A1 | 11/2001 | Lorch et al. | |
| 2006/0002823 A1* | 1/2006 | Feldstein | ..................... 422/100 |

FOREIGN PATENT DOCUMENTS

| | | | |
|---|---|---|---|
| EP | 1324019 A1 * | 7/2003 | |
| EP | 1 385 006 A2 | 1/2004 | |
| JP | 4084738 A | 3/1992 | |
| JP | 6-167443 A | 6/1994 | |
| JP | 2000-65731 A | 3/2000 | |
| JP | 2000097844 A | 4/2000 | |
| JP | 2002090289 A | 3/2002 | |
| JP | 2003527580 T | 9/2003 | |
| JP | 2004053372 A | 2/2004 | |
| WO | 9705492 A1 | 2/1997 | |
| WO | WO 2004/059301 A1 | 7/2004 | |

OTHER PUBLICATIONS

Takayuki Okamoto, "Surface Refracto-Sensor using Evanescent Waves: Principles", Spectrum Researches, 1998, pp. 19-28, vol. 47, No. 1.
Danny Van Noort, et al., "Porous Gold in Surface Plasmon Resonance Measurement", Eurosensors XIII, Sep. 12-15, 199, pp. 585-588.
P. I. Nikitin, et al., "Surface Plasmon Resonance Interferometry for Micro-Array Biosensing", Eurosensors XIII, Sep. 12-15, 1999, pp. 235-238.

* cited by examiner

*Primary Examiner*—Gregory J Toatley, Jr.
*Assistant Examiner*—Amanda H Merlino
(74) *Attorney, Agent, or Firm*—Sughrue Mion, PLLC

(57) ABSTRACT

A measuring unit for use in a sensor utilizing the phenomenon of attenuation in total internal reflection includes a dielectric block which is transparent to a light beam and has a flat and smooth surface on which a film layer is formed, and a flow passage member held in close contact with the film layer. The flow passage member is provided with a passage comprising a supply passage extending from an inlet of the flow passage member to a measuring portion and a discharge passage extending from the measuring portion to an outlet of the flow passage member.

14 Claims, 13 Drawing Sheets

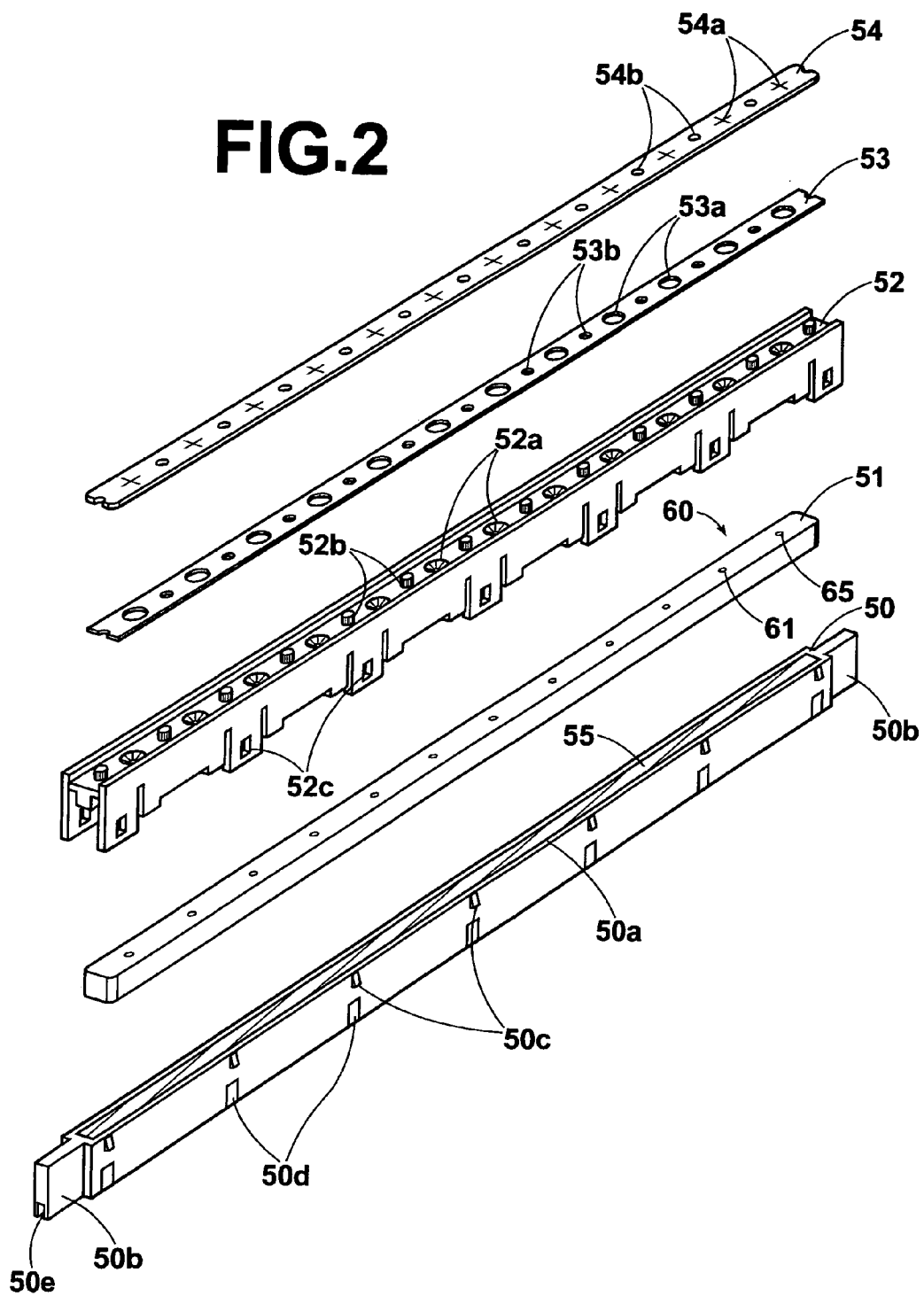

Figure 1:
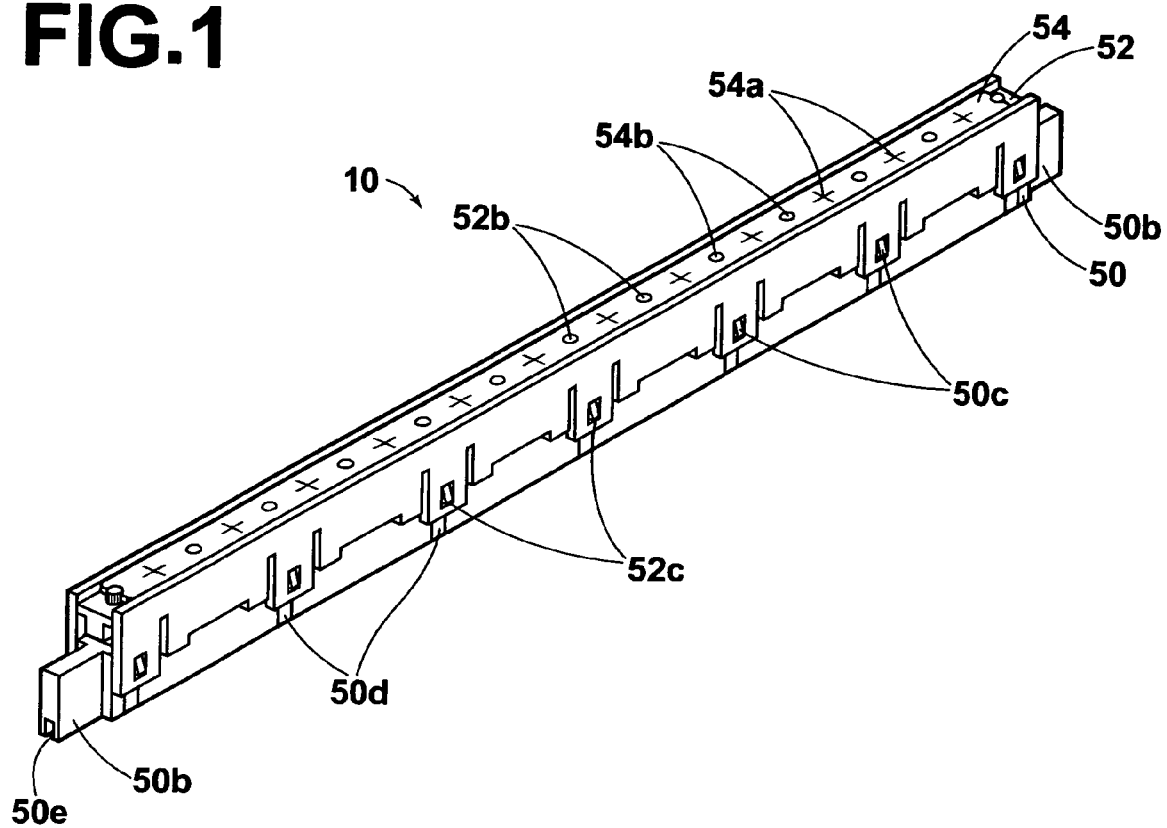

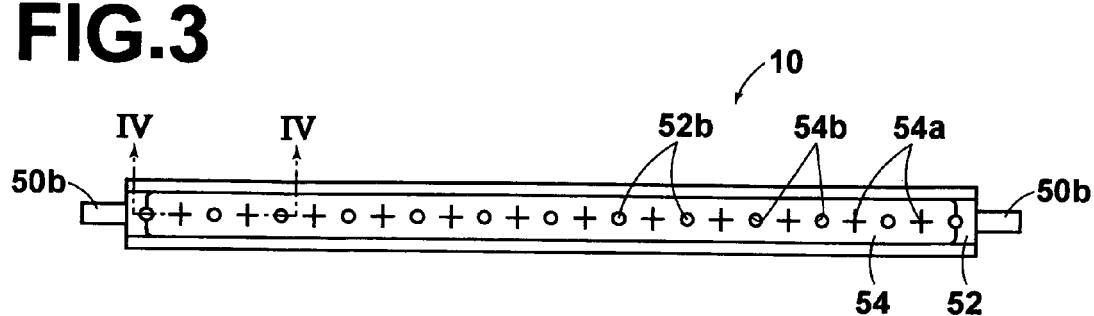
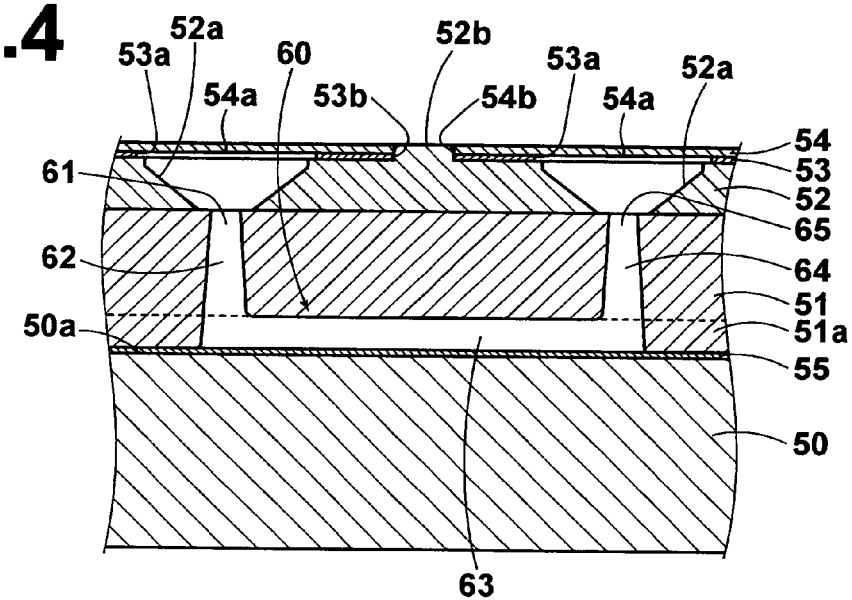

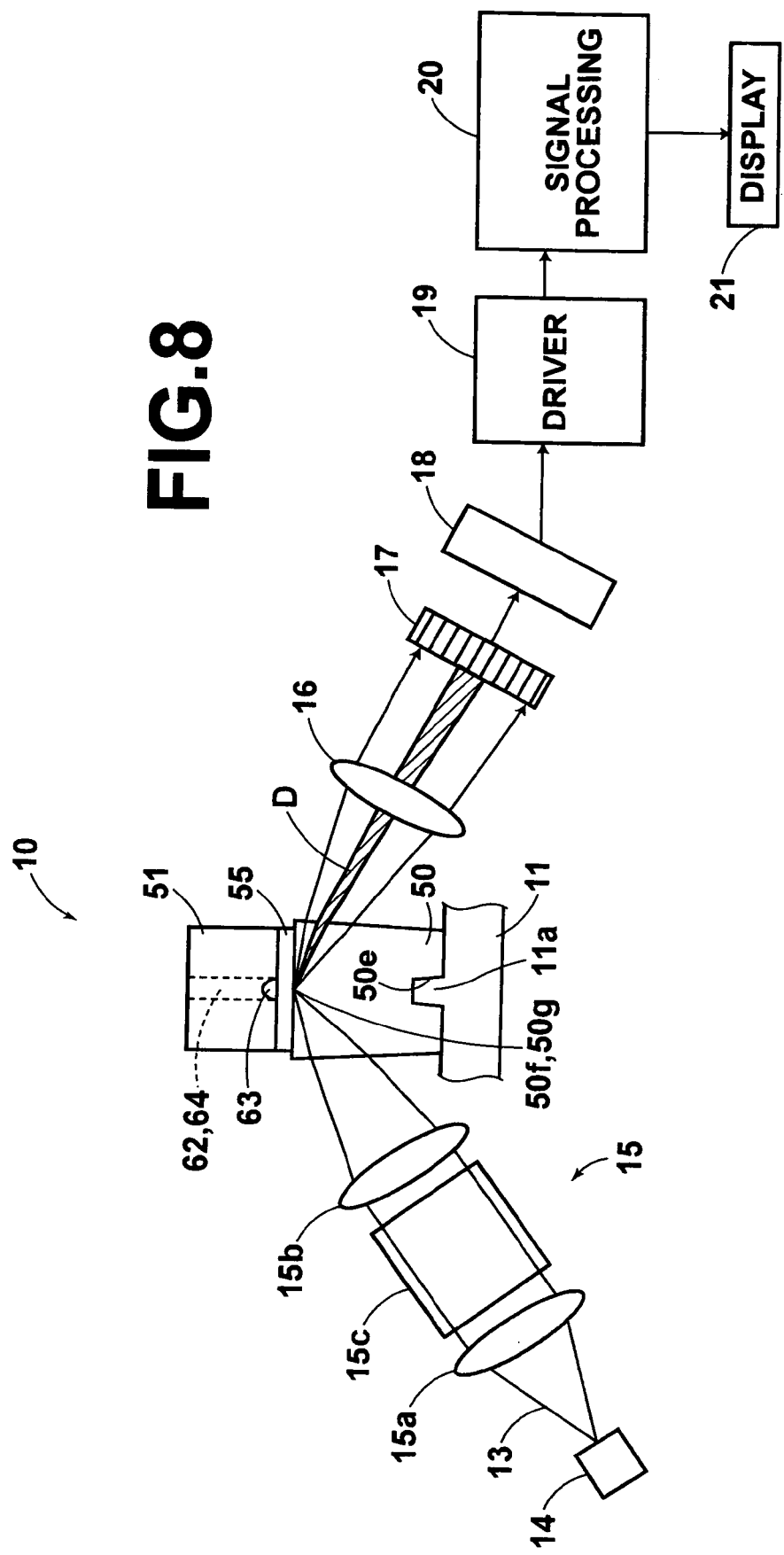

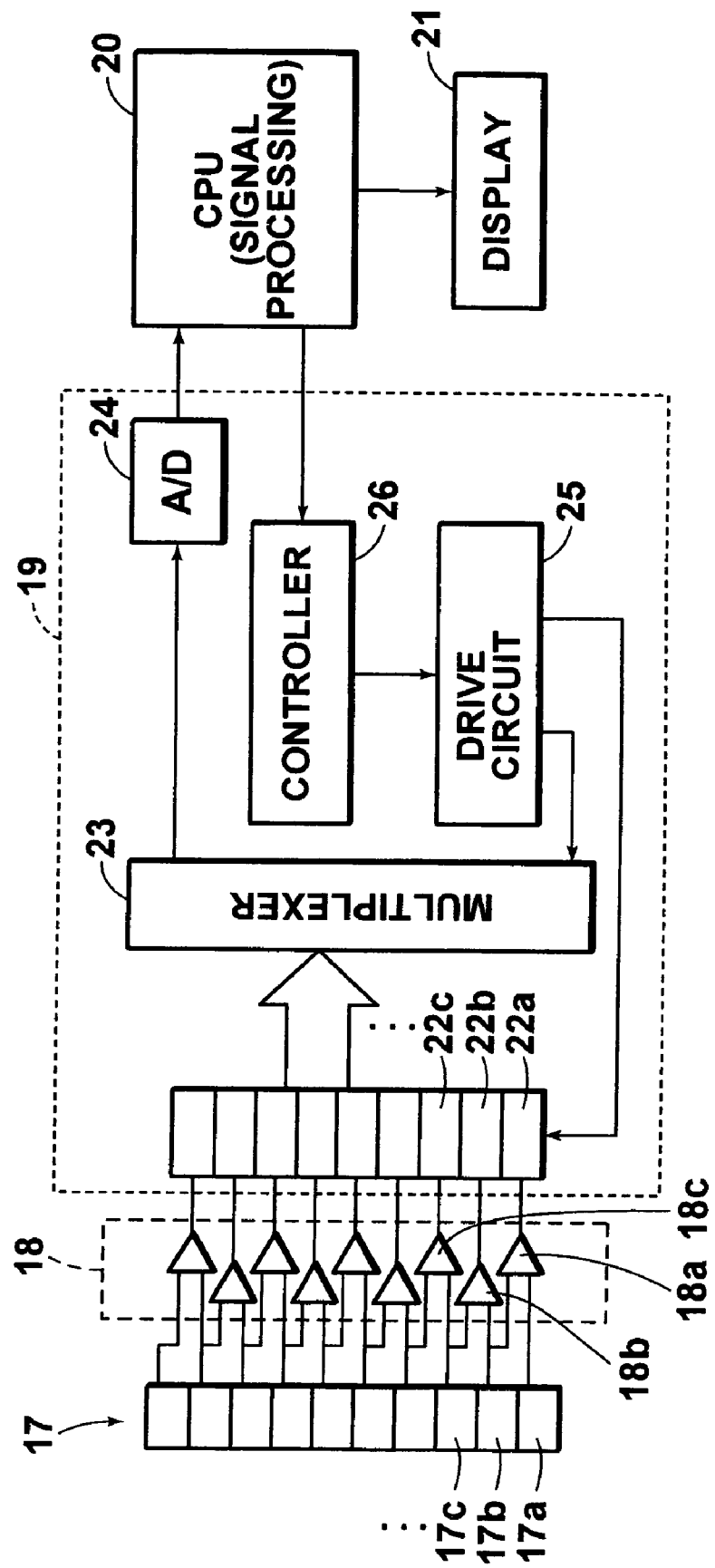

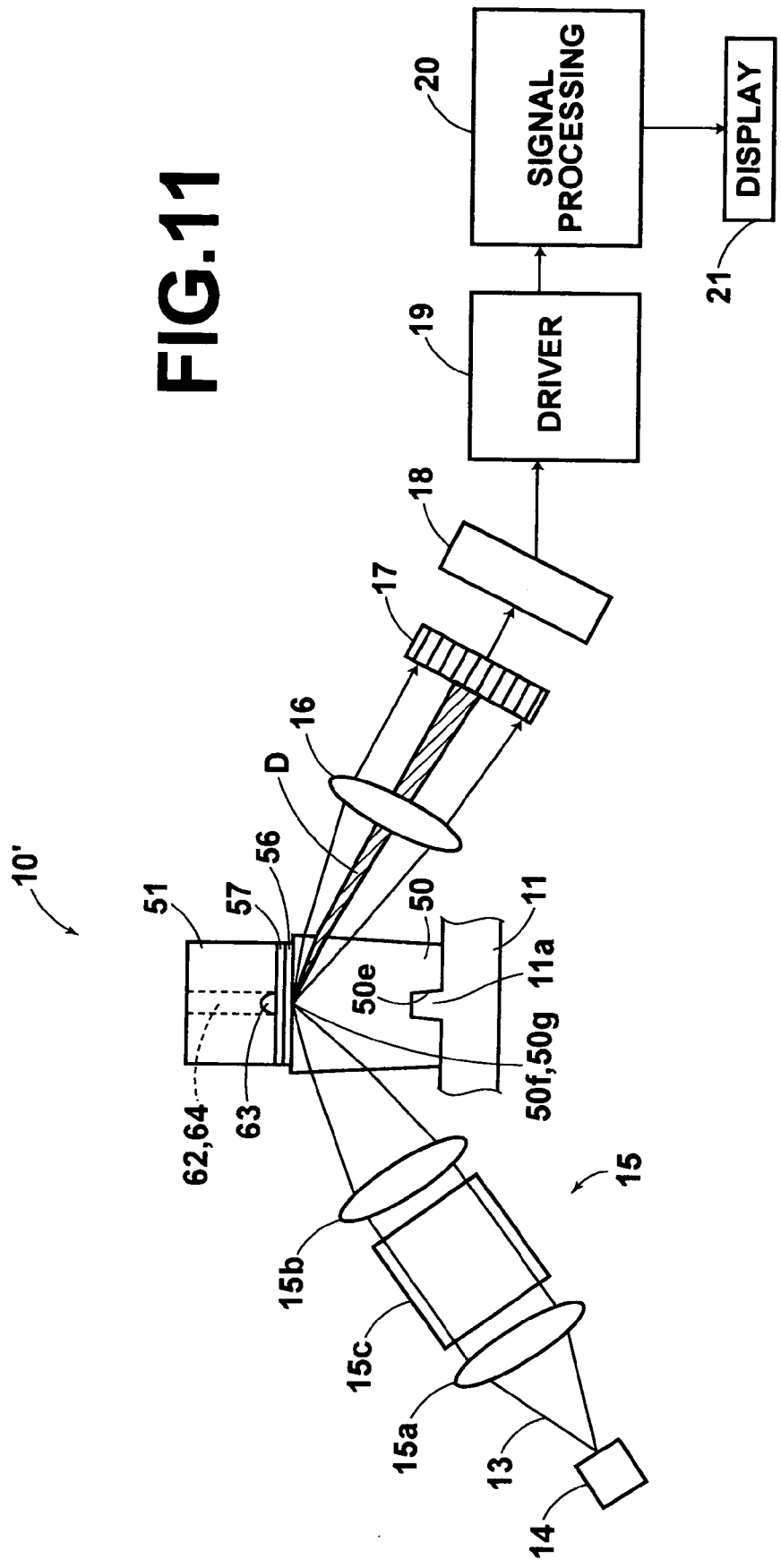

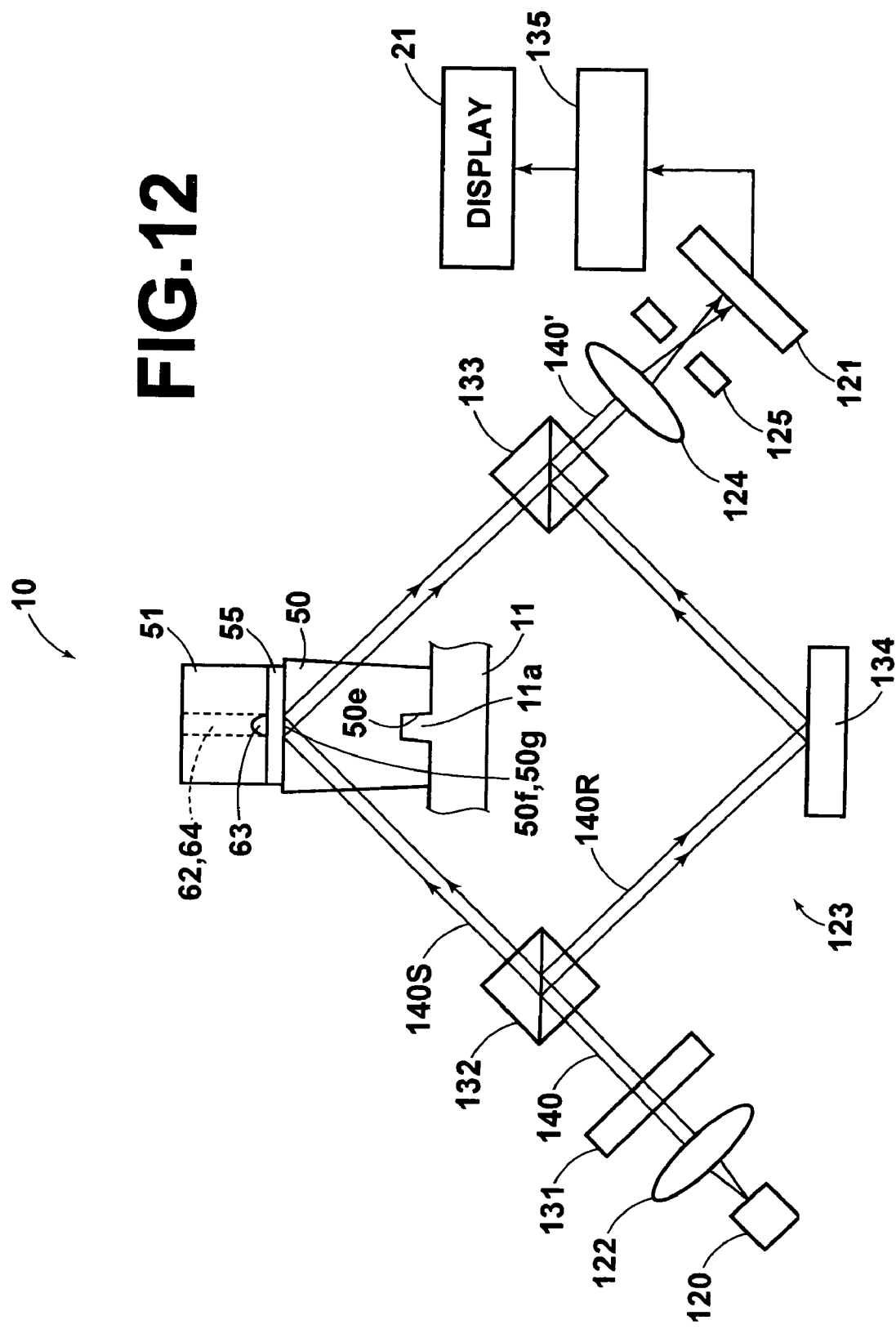

MEASURING UNIT

BACKGROUND OF THE INVENTION

1. Field of the Invention

This invention relates to a measuring unit for use in a sensor where a light beam is caused to be reflected in total internal reflection at an interface between a film layer in contact with an object to be measured such as a sample and a dielectric block to generate evanescent waves, and the change in the intensity of the light beam reflected in total internal reflection is measured to analyze the sample.

2. Description of the Related Art

As a measuring system using evanescent waves, there has been known a surface plasmon sensor. In metal, free electrons vibrate in a group to generate compression waves called plasma waves. The compression waves generated in a metal surface are quantized into surface plasmon. The surface plasmon sensor analyzes the property of the sample utilizing a phenomenon that such surface plasmon is excited by light waves. There have been proposed various types of surface plasmon sensors. Among those, one employing a system called "Kretschmann configuration" is best known. See, for instance, Japanese Unexamined Patent Publication No. 6(1994)-167443.

The plasmon resonance sensor using the Kretschmann configuration basically comprises a dielectric block shaped, for instance, like a prism, a metal film which is formed on one face of the dielectric block and is brought into contact with a sample, a light source emitting a light beam, an optical system which causes the light beam to enter the dielectric block to impinge upon the interface of the dielectric block and the metal film at various angles of incidence so that total internal reflection conditions are satisfied at the interface, and a photodetector means which detects the intensity of the light beam reflected in total internal reflection at the interface and a measuring means which detects a state of surface plasmon resonance on the basis of the result of detection of the photodetector means.

In order to obtain various angles of incidence of the light beam to the interface, a relatively thin incident light beam may be caused to impinge upon the interface while deflecting the incident light beam so that the angle of incidence changes or a relatively thick incident light beam may be caused to impinge upon the interface in the form of convergent light or divergent light so that components of the incident light beam impinge upon the interface at various angles. In the former case, the light beam which is reflected from the interface at an angle which varies as the incident light beam is deflected may be detected by a small photodetector which is moved in synchronization with deflection of the incident light beam or by an area sensor extending in the direction in which reflected light beam is moved as a result of deflection. In the latter case, the light beam which is reflected from the interface can be detected by an area sensor which extends in directions so that all the components of light reflected from the interface at various angles can be detected.

In such a plasmon resonance sensor, when a light beam impinges upon the interface at a particular angle of incidence θsp not smaller than the angle of total internal reflection, evanescent waves having an electric field distribution in the sample in contact with the metal film are generated and surface plasmon is excited in the interface between the metal film and the sample by the evanescent waves. When the wave number vector of the evanescent waves is equal to the wave number of the surface plasmon and wave number matching is established, the evanescent waves and the surface plasmon resonate and light energy is transferred to the surface plasmon, whereby the intensity of light reflected in total internal reflection at the interface of the dielectric block and the metal film sharply drops. The sharp intensity drop is generally detected as a dark line by the photodetector.

The aforesaid resonance occurs only when the incident light beam is p-polarized. Accordingly, it is necessary to set the light beam to impinge upon the interface in the form of p-polarized light.

When the wave number of the surface plasmon can be known from the angle of incidence θsp at which the phenomenon of attenuation in total internal reflection (ATR) takes place, the dielectric constant of the sample can be obtained. That is, $$K_{sp}(\omega) = \frac{\omega}{c} \sqrt{\frac{\varepsilon_m(\omega)\varepsilon_s}{\varepsilon_m(\omega)+\varepsilon_s}}$$

wherein $K_{sp}$ represents the wave number of the surface plasmon, ω represents the angular frequency of the surface plasmon, c represents the speed of light in a vacuum, and $\varepsilon_m$ and $\varepsilon_s$ respectively represent the dielectric constants of the metal and the sample.

When the dielectric constant $\varepsilon_s$ of the sample is known, the refractive index of the sample and the like can be calculated on the basis of a predetermined calibration curve and the like and accordingly a property related to the dielectric constant $\varepsilon_s$ of the sample or the refractive index of the sample can be detected by detecting the angle of incidence θsp at which the intensity of light reflected in total internal reflection from the interface of the prism and the metal film sharply drops (this angel θsp will be referred to as "the attenuation angle θsp", hereinbelow).

As a similar apparatus utilizing the evanescent waves, there has been known a leaky mode sensor described in, for instance, "Surface Refracto-sensor using Evanescent Waves: Principles and Instrumentations", by Takayuki Okamoto, Spectrum Researches, Vol.47, No.1, 1998, pp.19-28. The leaky mode sensor basically comprises a dielectric block shaped, for instance, like a prism, a clad layer which is formed on one face of the dielectric block, an optical waveguide layer which is formed on the clad layer and is brought into contact with a sample, a light source emitting a light beam, an optical system which causes the light beam to enter the dielectric block to impinge upon the interface of the dielectric block and the metal film at various angles of incidence so that total internal reflection conditions are satisfied at the interface, and a photodetector means which detects the intensity of the light beam reflected in total internal reflection at the interface and a measuring means which detects a state of excitation of the waveguide mode on the basis of the result of detection of the photodetector means.

In the leaky mode sensor with this arrangement, when the light beam is caused to impinge upon the clad layer through the dielectric block at an angle not smaller than an angle of total internal reflection, only light having a particular wave number and impinging upon the optical waveguide layer at a particular angle of incidence comes to propagate through the optical waveguide layer in a waveguide mode after passing through the clad layer. When the waveguide mode is thus excited, almost all the incident light is taken in the optical waveguide layer and accordingly, the intensity of light reflected in total internal reflection at the interface of the dielectric block and the clad layer sharply drops. That is, attenuation in total internal reflection occurs. Since the wave number of light to be propagated through the optical waveguide layer in a waveguide mode depends upon the refractive index of the sample on the optical waveguide layer, the refractive index and/or the properties of the sample related to the refractive index can be detected on the basis of the angle of incidence θsp at which the attenuation in total internal reflection occurs.

The surface plasmon sensor and the leaky mode sensor are sometimes used in random screening for finding a specific material combined with a predetermined sensing material in the field of pharmacy or the like. In this case, a sensing material is fixed on the film layer (the metal film in the case of the surface plasmon sensor, and the clad layer and the optical waveguide layer in the case of the leaky mode sensor), and a sample liquid containing a material to be analyzed is spotted on the sensing material. Then the attenuation angle θsp is repeatedly measured each time a predetermined time lapses.

When the sample material (the material to be analyzed) in the sample liquid is combined with the sensing material, the refractive index of the sensing material changes with time due to combination with the sample material. Accordingly, by measuring the attenuation angle θsp, at which attenuation in total internal reflection takes place, for every predetermined time, thereby detecting whether the attenuation angle θsp changes, it is possible to know whether the sample material is a specific material to be combined with the sensing material. As combinations of such a specific material and a sensing material, there have been known combinations of antigens and an antibodies and of antibodies and other antibodies. For example, rabbit antihuman IgG antibody is fixed on the surface of the film layer as the sensing material with human IgG antibody employed as the specific material.

In order to detect the state of combination of the sample material with the sensing material, the total reflection attenuation angle θsp itself need not necessarily be detected. For example, the amount of change in the total reflection attenuation angle θsp after the sample liquid is spotted onto the sensing material is measured and the state of combination of the sample material with the sensing material may be measured on the basis of the amount of change of the total reflection attenuation angle θsp.

As the sensors, there has been known those where the liquid sample is continuously supplied by the use of a flow passage mechanism to a flat-plate-like measuring chip to which a sensing material is fixed. (See, for instance, Japanese Unexamined Patent Publication No. 2000-065731.) When a sensor of this type is used, the state of combination can be accurately measured since a new liquid sample is always supplied to the measuring chip every time the state of combination of the sample material with the sensing material is measured and the concentration of the sample material in the liquid sample does not change. When there is a combination of the sensing material and a specific material, the state of dissociation of the sensing material and the specific material can be measured by flowing a liquid sample free from the specific material onto the measuring chip to which the combination is fixed. Further, for instance, when gas is used as the sample, or a liquid sample in which gas is dissolved is used, the sample can be easily supplied to the measuring chip by the use of the flow passage mechanism.

Further, recently, in response to advent of variety of sensing reactions, various solvents have come to be used as the solvent for the sample material and these solvents include solvents which are relatively volatile such as water. Evaporation of water at this time means change in the refractive index of the liquid sample and since the measuring signal changes, an accurate measurement sometimes becomes difficult. By providing the flow passage mechanism, evaporation of the solvent of the liquid sample can be minimized and the measuring signal can be stabilized.

Though various merits can be obtained by providing the flow passage mechanism, providing the flow passage mechanism is disadvantageous in that long piping becomes necessary and a lot of liquid sample is required to supply a sample material to the measuring chip.

SUMMARY OF THE INVENTION

In view of the foregoing observations and description, the primary object of the present invention is to provide a measuring unit for use in a sensor using evanescent waves which is provided with a flow passage mechanism for supplying the sample onto the film layer and permits reduction of the sample required for measurement.

In accordance with the present invention, there is provided a measuring unit comprising a dielectric block which is transparent to a light beam and has a flat and smooth surface on which a film layer is formed, and a flow passage member held in close contact with the film layer, wherein the flow passage member is provided with a passage comprising a supply passage extending from an inlet of the flow passage member to a measuring portion and a discharge passage extending from the measuring portion to an outlet of the flow passage member.

In the measuring unit of the present invention, the film layer may comprise metal film so that the measuring unit of the present invention forms a measuring unit for use in a surface plasmon sensor which measures on the basis of the surface plasmon resonance effect or may comprise a clad layer which is formed on one face of the dielectric block and an optical waveguide layer which is formed on the clad layer so that the measuring unit of the present invention forms a measuring unit for use in a leaky mode sensor which measures on the basis of the effect of excitation of the optical waveguide mode in the optical waveguide layer.

The dielectric block may be shaped like a plate without a prism which causes a light beam emitted from the light source of the sensor to impinge upon the interface between the dielectric block and the film layer and causes the light beam reflected in total internal reflection at the interface to impinge upon the photodetector of the sensor, or may be formed integrally with such a prism.

Further, it is preferred that the flow passage member be formed by an elastic material. In this case, it is further preferred that the flow passage member be provided with a slit portion or a septum portion at its inlet portion and/or outlet portion. The slit portion or the septum portion need not be positioned just at the end of the inlet portion and/or the outlet portion but may be positioned near the inlet and/or the outlet.

It is further preferred that the measuring unit of the present invention be further provided with a holding member which is engaged with the dielectric block to hold the flow passage member on one surface of the dielectric block. In this case, the holding member is provided with a holding plate portion which is held in close contact with the surface of the flow passage member in which each of the inlet and the outlet is formed, and the holding plate portion is preferred that a tapered insertion hole tapered toward the flow passage member (becomes smaller toward the flow passage member) be provided in a position opposed to the inlet or the outlet of the flow passage member.

It is further preferred that the measuring unit of the present invention be further provided with an evaporation preventing member which seals the inlet and/or the outlet of the flow passage member and prevents the sample from being evaporating. In this case, the evaporation preventing member may be formed by an elastic material and may be formed with a slit in a position opposed to the inlet and/or the outlet of the flow passage member. The holding member and the evaporation preventing member may be formed integrally with each other or may be bonded together by an adhesive.

Further, the flow passage member may be provided with a plurality of the flow passages. In this case, the flow passages may be linearly arranged or may be arranged like a matrix.

When measuring an object to be measured such as a sample by the use of the measuring unit of this embodiment, that is, when information on the refractive index of the object to be measured is to be obtained by the use of the measuring unit of this embodiment, the refractive index of the sample on the film layer itself may be obtained or a sensing material such as an antibody may be fixed to the film layer so that change of the refractive index or existence of change of the refractive index due to, for instance, antigen-antibody reaction is obtained.

The information on the refractive index may be obtained by detecting the light beam caused to impinge upon the interface between the dielectric block and the film layer at various angles and reflected at the same to obtain the attenuation angle or change of the attenuation angle or may be obtained by causing light beams of different wavelengths to enter the dielectric block to impinge upon the interface of the dielectric block and the metal film at various angles of incidence so that total internal reflection conditions are satisfied at the interface and detecting the intensity of the light beam reflected at the interface by the wavelengths to detect the attenuation angle by the wavelengths and obtaining the refractive index or change of the refractive index on the basis of the intensity of the light beam reflected at the interface by the wavelengths as disclosed in "Porous Gold in Surface Plasmon Resonance Measurement", by D. V. Noort et al., EUROSENSORS XIII, 1999, pp.585-588. Further as disclosed in "Surface Plasmon Resonance Interferometry for Micro-Array Biosensing", by P. I. Nikitin et al., EUROSENSORS XIII, 1999, pp.235-238, change of the refractive index may be obtained by causing a light beam to enter the dielectric block to impinge upon the interface of the dielectric block and the metal film at various angles of incidence so that total internal reflection conditions are satisfied at the interface, splitting a part of the light beam before the light beam impinges upon the interface, causing the split part of the light beam to interfere with the light beam reflected at the interface and detecting change of the interference fringes of the light beams.

That is, the information on the refractive index of the object to be measured may be any so long as it changes with the refractive index of the object to be measured. For example, it may be on an attenuation angle which changes with the refractive index of the object to be measured, a wavelength of the light beam which generates attenuation in total internal reflection, change of the attenuation angle, change of the wavelength of the light beam which generates attenuation in total internal reflection or change of the interference fringes.

In accordance with the measuring unit of the present invention, since the flow passage member is provided with a passage comprising a supply passage extending from an inlet of the flow passage member to a measuring portion and a discharge passage extending from the measuring portion to an outlet of the flow passage member and the liquid sample can be directly supplied from the inlet of the flow passage member by the use of an external liquid feed component such as a pipette chip, the measuring unit is provided with a flow passage mechanism for supplying the sample onto the film layer and at the same time, long piping which has been necessary in the past becomes unnecessary to permit reduction of the sample required for measurement.

Further, when the flow passage member is formed by an elastic material, the flow passage member can be surely brought into close contact with the film layer and leakage of the liquid sample through the contact surface can be prevented. Further, when the flow passage member is further provided with a slit portion or a septum portion at its inlet portion and/or outlet portion, evaporation of the liquid sample can be prevented and change of the refractive index of the sample due to evaporation of the liquid sample can be prevented, whereby the measuring signal can be stabilized.

Further, when the measuring unit of the present invention is further provided with a holding member which is engaged with the dielectric block to hold the flow passage member on one surface of the dielectric block, handleability of the measuring unit can be improved since the dielectric block and the flow passage member can be separated from each other, for instance, during transportation. In this case, when the holding member is provided with a holding plate portion which is held in close contact with the surface of the flow passage member in which each of the inlet and the outlet is formed, and a tapered insertion hole which becomes smaller toward the flow passage member is provided in the holding member in a position opposed to the inlet or the outlet of the flow passage member, an external liquid feed component such as a pipette or a syringe can be easily inserted into the inlet or the outlet of the flow passage member.

Further, when the measuring unit of the present invention is further provided with an evaporation preventing member which seals the inlet and/or the outlet of the flow passage member and prevents the sample from being evaporating, change of the refractive index of the sample due to evaporation of the liquid sample can be prevented, and accordingly the measuring signal can be stabilized. In this case, when the evaporation preventing member is formed by an elastic material and is formed with a slit in a position opposed to the inlet and/or the outlet of the flow passage member, the evaporation preventing member can be made in a simple structure.

When the holding member and the evaporation preventing member is formed integrally with each other, the number of components can reduced and accordingly, the productivity of the measuring unit can be improved.

When the holding member and the evaporation preventing member is bonded together by an adhesive, the former and the latter can be formed in different materials.

When the flow passage member is provided with a plurality of flow passages, measurement on a plurality of samples can be simultaneously done in parallel with a single measuring unit.

BRIEF DESCRIPTION OF THE DRWAINGS

Figure 5:
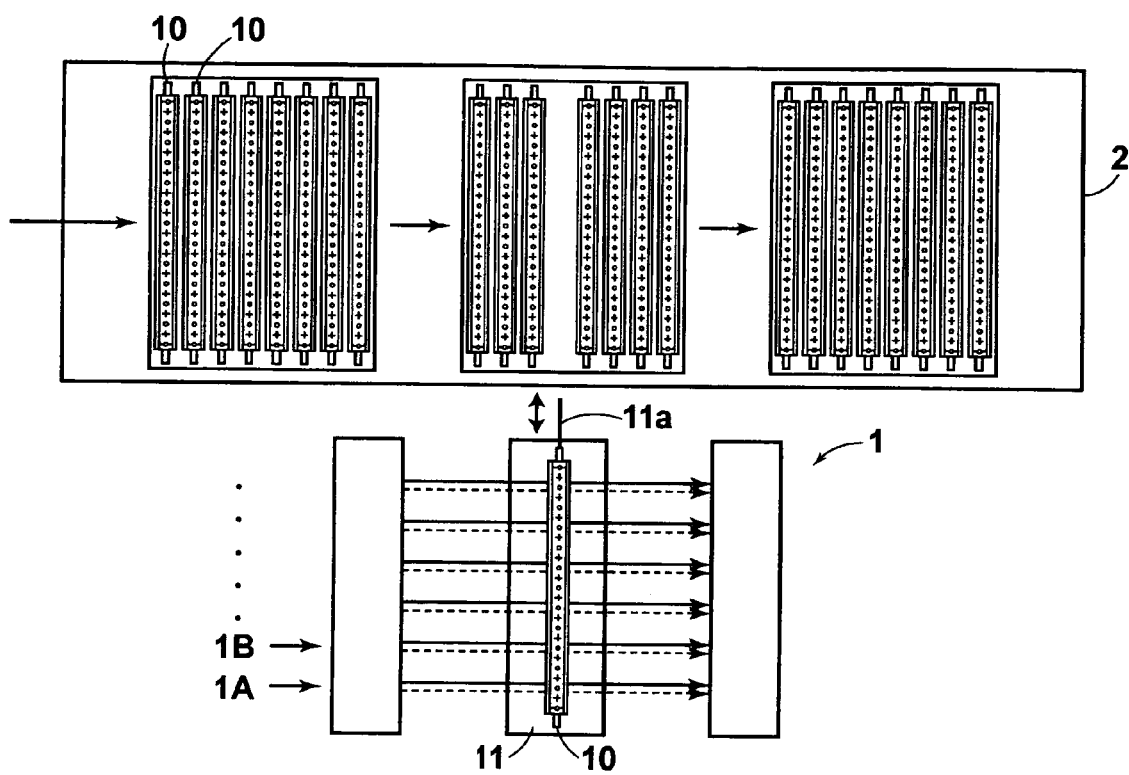
Figure 6:
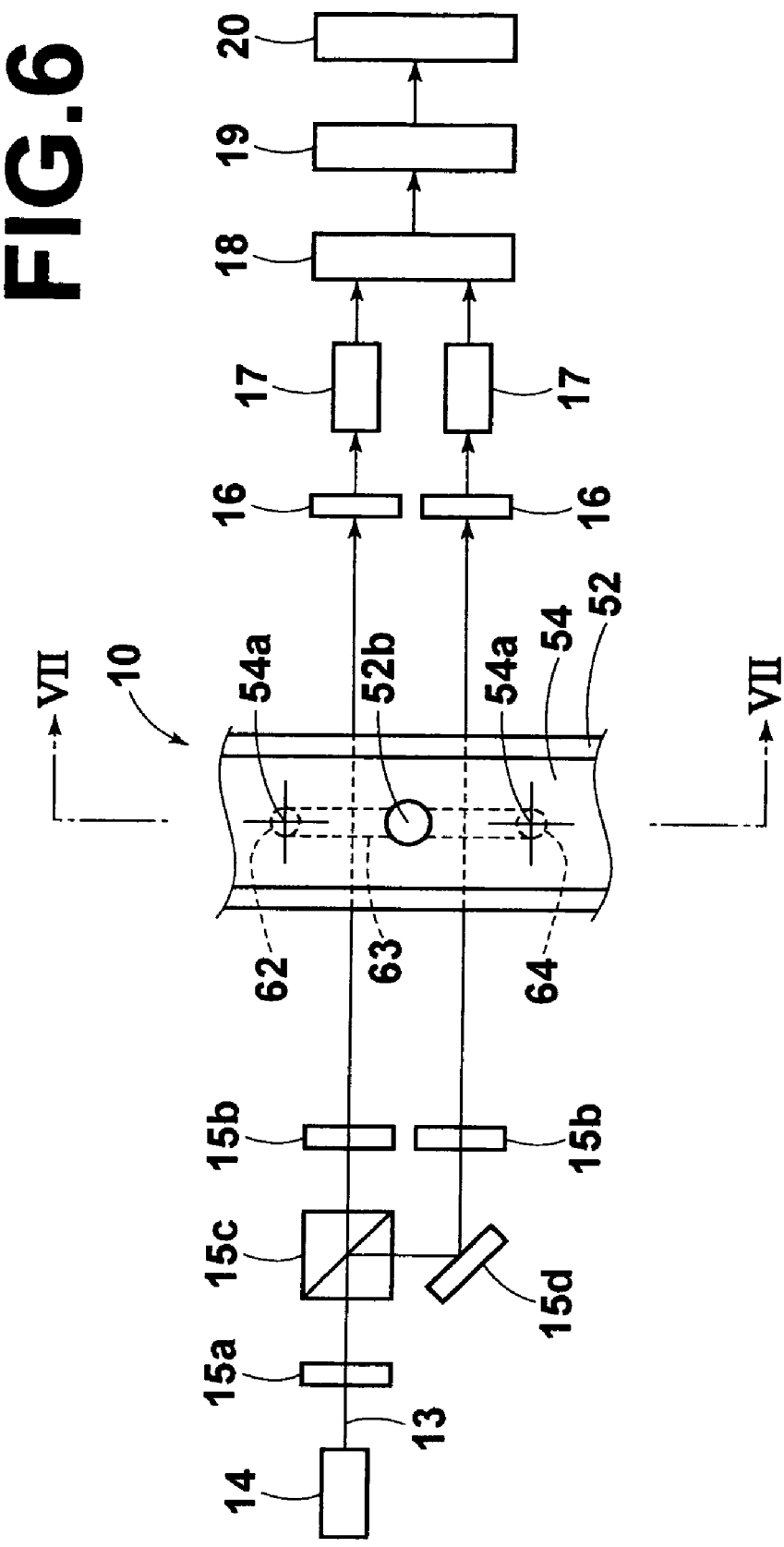
Figure 7:
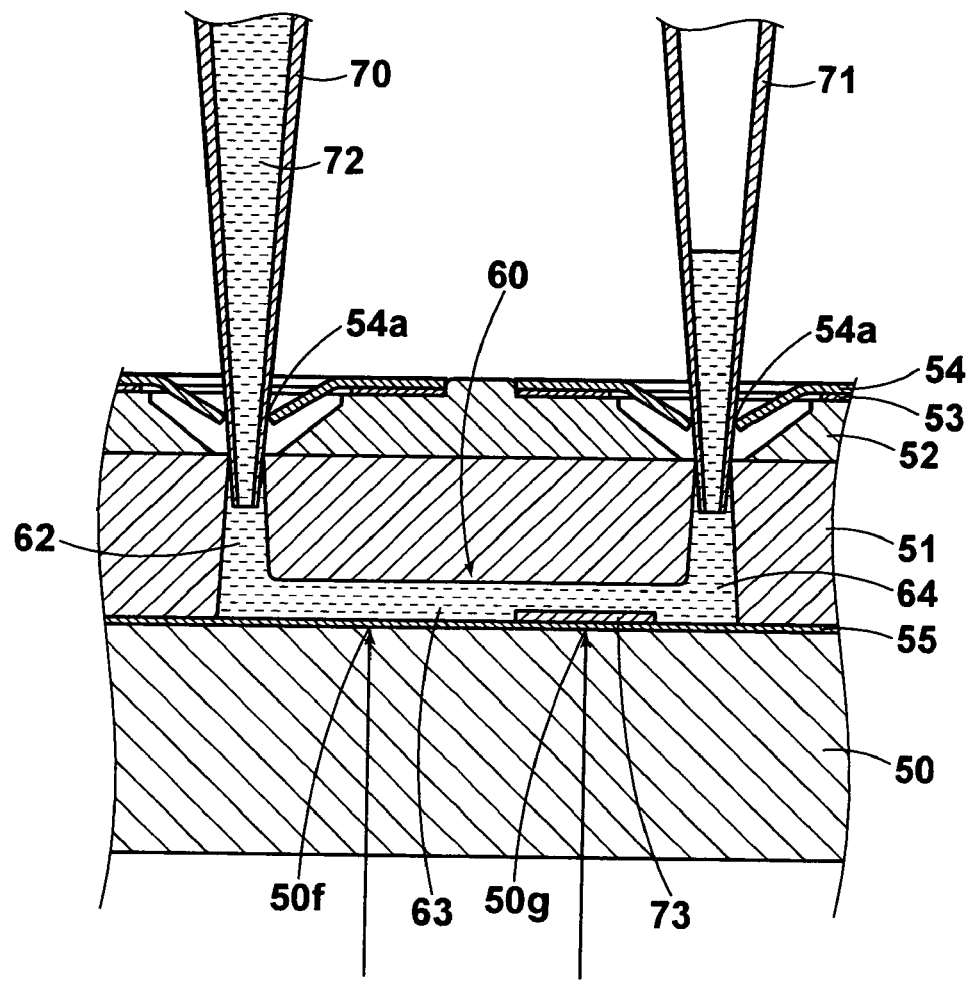
Figure 10A:
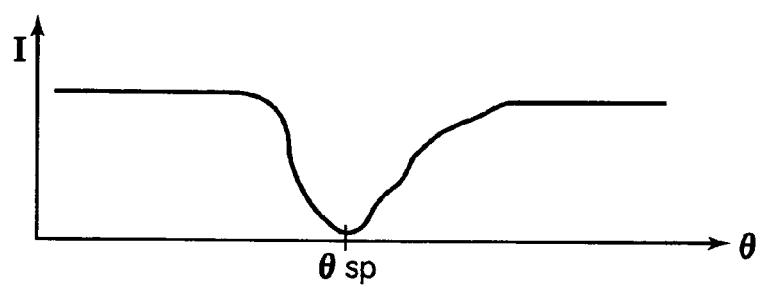
Figure 10B:
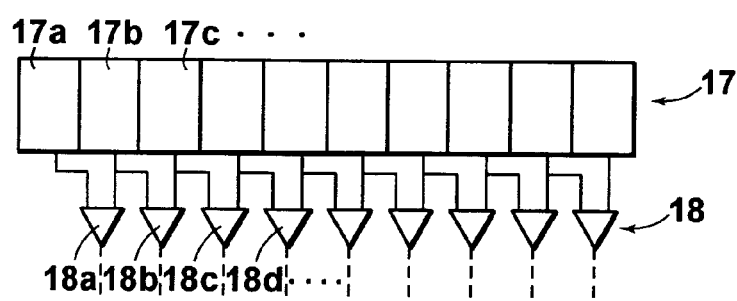
Figure 10C:
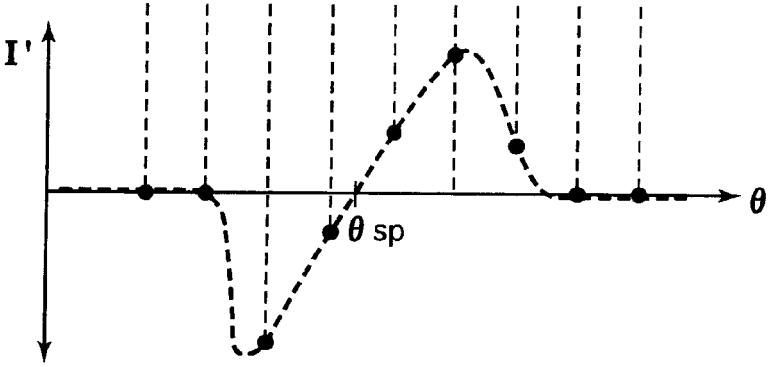
Figure 13A:
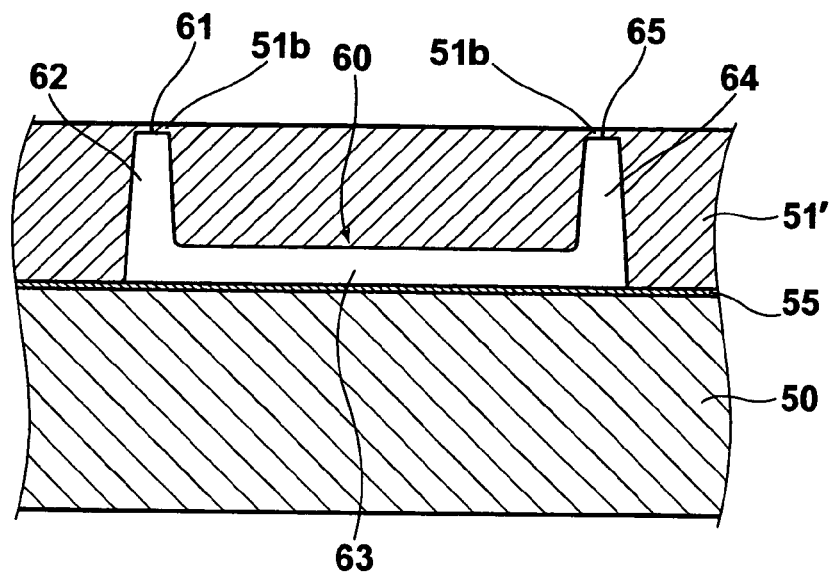
Figure 13B:
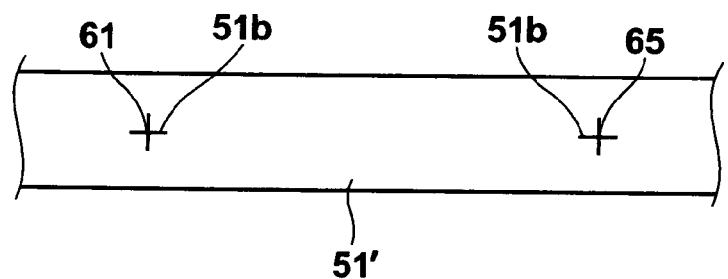
Figure 14A:
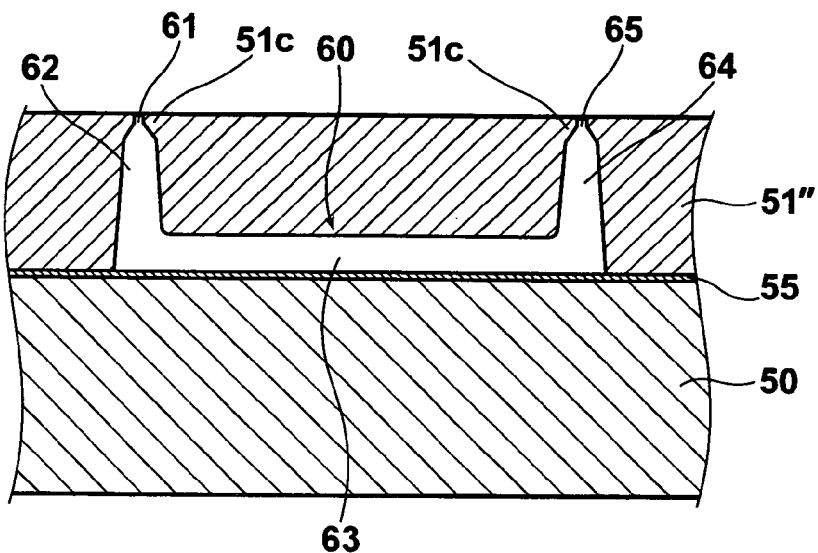
Figure 14B:
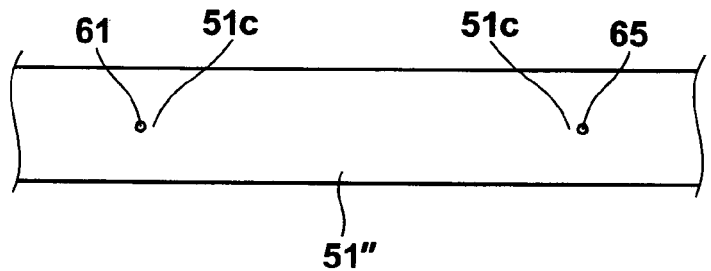
Figure 15:
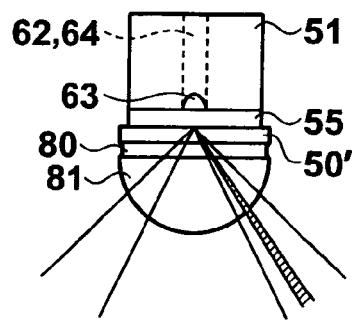

FIG. 1 is a perspective view of a measuring unit in accordance with a first embodiment of the present invention, FIG. 2 is an exploded perspective view of the measuring unit, FIG. 3 is a plan view of the measuring unit, FIG. 4 is a cross-sectional view taken along line IV-IV in FIG. 3, FIG. 5 is a fragmentary plan view showing a part of a surface plasmon resonance sensor employing the measuring plate in accordance with the first embodiment of the present invention, FIG. 6 is a plan view of the measuring system of the surface plasmon resonance sensor, FIG. 7 is a cross-sectional view taken along line VII-VII in FIG. 6, FIG. 8 is a side view of the measuring system of the surface plasmon resonance sensor, FIG. 9 is a block diagram showing an electric arrangement of the measuring system of the surface plasmon resonance sensor, FIGS. 10A, 10B and 10C are graphs for illustrating the relation between the angle of incidence of light to the interface and the intensity of the reflected light beam detected in the measuring system of the surface plasmon resonance sensor, and the relation between the angle of incidence of light to the interface and the differentiation of the light intensity detecting signal, FIG. 11 is a side view of the measuring system of a leaky mode sensor employing a measuring plate in accordance with a second embodiment of the present invention, FIG. 12 is a side view of the measuring system of a surface plasmon resonance sensor employing a measuring plate in accordance with a third embodiment of the present invention, FIG. 13A is a fragmentary longitudinal cross-sectional view of a measuring unit in accordance with another embodiment of the present invention, FIG. 13B is a fragmentary plan view of the same, FIG. 14A is a fragmentary longitudinal cross-sectional view of a measuring unit in accordance with still another embodiment of the present invention, FIG. 14B is a fragmentary plan view of the same, and FIG. 15 is a transverse cross-sectional view of a measuring unit in accordance with still another embodiment of the present invention.

DESCRIPTION OF THE PREFERRED EMBODIMENTS

In FIGS. 1 to 4, the measuring unit 10 comprises a dielectric block 50 which is transparent to a light beam and has a flat and smooth upper surface 50a on which a metal film layer 55 is formed, a flow passage member 51 held in close contact with the metal film layer 55, and a holding member 52 which is engaged with the dielectric block 50 to hold the flow passage member 51 on the upper surface 50a of the dielectric block 50.

The dielectric block 50 is formed, for instance, by transparent resin and has a body shaped like a trapezoid where the lower side is shorter than the upper side in a cross-section perpendicular to the longitudinal direction. The dielectric block 50 is formed with a holding portion 50b on each end of the body and formed integrally with a prism portion which causes the light beam emitted from the light source of a measuring system to be described later to impinge upon the interface of the dielectric block 50 and the metal film 55 and causes the light beam reflected at the interface in total internal reflection to emit toward the photodetector means of the measuring system. The holding portion 50b of the dielectric block 50 is thinner than the body of the dielectric block 50 as seen from above or from below. Engagement projections 50c which are to be engaged with an engagement hole 52c on the holding member 52 to be described later and perpendicular projections 50d which are perpendicular in their side surfaces are formed on the longitudinal side surfaces of the body of the dielectric block 50 to be opposed to each other on each side surfaces of the body of the dielectric block 50, and a sliding groove 50e is formed on the bottom of the body of the dielectric block 50 to extend in parallel to the longitudinal direction thereof.

In the flow passage member 51, a plurality of flow passages 60, each comprising a supply passage 62 from an inlet 61 to a measuring portion 63 and a discharge passage 64 from the measuring portion 63 to an outlet 65, are formed and linearly arranged in the longitudinal direction of the flow passage member 51.

As shown in FIG. 4, the outlet of the supply passage 62 and the inlet of the discharge passage 64 open in a lower portion of the flow passage member 51, and a seal portion 51a circumscribing the outlet of the supply passage 62 and the inlet of the discharge passage 64 is formed in an area of the flow passage member 51 which is positioned in the bottom surface of the flow passage member 51 and is brought into contact with the surface of the metal film 55. The inner side of the seal portion 51a forms the measuring portion 63. Accordingly, when the flow passage member 51 is held in close contact with the metal film 55 on the dielectric block 50, the measuring portion 63 in the seal portion 51a comes to function as a flow passage. The seal portion 51a may be formed integrally with an upper portion of the flow passage member 51 or may be formed by a material different from the upper portion of the flow passage member 51 and may be subsequently attached to the upper portion of the flow passage member 51. For example, the seal portion 51a maybe an O-ring attached to the upper portion of the flow passage member 51.

In a measuring system such as a surface plasmon resonance sensor employing the measuring unit of this embodiment, that a liquid sample containing therein protein is used is expected. Since it is difficult to effect the measurement when protein is fixed to the flow passage 60, it is preferred that the flow passage member 51 be formed by a material which does not exhibit non-specific adsorption to proteins. For example, it is preferred that the flow passage member 51 is formed by silicone or polypropylene. Further, by forming the flow passage member 51 by an elastic material, the flow passage member 51 can be surely held in close contact with the metal film 55 and the leakage of the liquid sample through the contact surface can be prevented.

The holding member 52 is formed of an elastic material such as polypropylene and is substantially U-shaped in cross-section transverse to the longitudinal direction thereof and is formed in a position opposed to the inlet 61 or the outlet 65 of the flow passage member 51 in the upper plate (the holding plate portion) thereof with tapered pipette insertion holes 52a which taper toward the flow passage member 51. Locator bosses 52 bare formed in the upper surface of the holding member 52 between the pipette insertion holes 52a and outside the pipette insertion holes 52a at the ends of the row of the pipette insertion holes 52a.

Further, an evaporation preventing member 54 is applied to the upper surface of the holding member 52 with double-coated tape (adhesive member) 53. As shown in FIG. 2, the double-coated tape 53 is provided with holes 53a and 53b respectively in positions opposed to the pipette insertion holes 52a and the locator bosses 52b. Similarly, the evaporation preventing member 54 is provided with slits 54a and holes 54b respectively in positions opposed to the pipette insertion holes 52a and the locator bosses 52b. With the locator bosses 52b inserted in the holes 53b of the double-coated tape 53 and the holes 54b of the evaporation preventing member 54, the evaporation preventing member 54 is applied to the upper surface of the holding member 52, whereby the slits 54a of the evaporation preventing member 54 are opposed to the inlets 61 and the outlets 65 of the flow passage member 51. It is necessary to form the evaporation preventing member 54 by an elastic material so that a pipette can be inserted through the silts 54a and the evaporation preventing member 54 is formed, for instance, by silicone or polypropylene. The holding member 52 and the evaporation preventing member 54 may be formed integrally with each other and in addition, the flow passage member 51 may be formed integrally with the holding member 52 and the evaporation preventing member 54.

The engagement holes 52c adapted to be engaged with the engagement projections 50c of the dielectric block 50 are formed in the longitudinal side plates of the holding member 52, and the holding member 52 is mounted on the dielectric block 50 with the engagement holes 52c engaged with the engagement projections 50c so that the flow passage member 51 is sandwiched between the holding member 52 and the dielectric block 50 and held on the upper surface 50a of the dielectric block 50.

As shown in FIG. 4, in a state where the flow passage member 51 is sandwiched between the holding member 52 and the dielectric block 50, the inlets 61 and the outlets 65 of the flow passage member 51 are isolated from the atmosphere by the evaporation preventing member 54 and the liquid sample injected into the flow passage 60 is prevented from evaporating.

A surface plasmon resonance sensor employing the measuring unit 10 of this embodiment will be described, hereinbelow. FIG. 5 is a fragmentary plan view showing a part of a surface plasmon resonance sensor employing the measuring plate in accordance with the first embodiment of the present invention, FIG. 6 is a plan view of the measuring system of the surface plasmon resonance sensor, FIG. 7 is a cross-sectional view taken along line VII-VII in FIG. 6, and FIG. 8 is a side view of the measuring system of the surface plasmon resonance sensor. In FIG. 8, the holding member 52 (including the double-coated tape 53 and the evaporation preventing member 54) is abbreviated.

As shown in FIG. 5, the surface plasmon resonance sensor 1 is a surface plasmon resonance sensor which can analyze a plurality of samples by entering light beams in parallel into a plurality of flow passages 60 formed in the measuring unit 10, and comprises a plurality of measuring systems 1A, 1B . . . which are the same in arrangement. Each measuring system will be described, hereinbelow, with the affixes A, B representing components of each measuring system abbreviated.

As shown in FIGS. 6 and 7, each of the measuring systems comprises a light source 14 formed, for instance, by a semiconductor laser generating a light beam 13 (will be simply referred to as "laser 14", hereinbelow), an incident optical system 15 which causes the light beams 13 to enter the measuring unit 10 in parallel to impinge upon the interfaces 50f and 50g of the dielectric block 50 and the metal film 55 (which are positioned below the flow passage 60) at various angles of incidence, a pair of collimator lenses 16 which respectively collimate the light beams 13 reflected at the respective interfaces 50f and 50g, a pair of photodiode arrays 17 which respectively detect the collimated light beams 13, a differential amplifier array 18 connected to the photodiode arrays 17, a driver 19, a signal processing portion 20 which may be, for instance, a computer system and a display portion 21 connected to the signal processing portion 20.

In this particular embodiment, the incident optical system 15 comprises a collimator lens 15a which collimates the light beam 13 emitted from the laser 14 as a divergent light beam, a half-silvered mirror 15c which splits the collimated light beam 13 into two light beams 13, a mirror 15d which reflects toward the measuring unit 10 the light beam 13 reflected by the half-silvered mirror 15c and a pair of condenser lenses 15b which converge the light beam 13 passing through the half-silvered mirror 15c and the light beam 13 reflected by the mirror 15d on the interfaces 50f and 50g.

Since converged as described above, the light beams 13 include components impinging upon the interfaces 50f and 50g at various angles of incidence θ. The angles of incidence θ are all not smaller than the angle of total internal reflection. Accordingly, the light beams 13 are reflected in total internal reflection at the interfaces 50f and 50g and the reflected light beams 13 include components reflected at the interfaces 50f and 50g at various angles of reflection. The incident optical system 15 may be arranged to cause the light beams 13 to impinge upon the interfaces 50f and 50g in a defocused state. This arrangement averages errors in detecting states of surface plasmon resonance and improves measuring accuracy.

The light beams 13 are caused to impinge upon the corresponding interfaces 50f and 50g in a p-polarized state. This can be realized by positioning the laser 14 so that its direction of polarization is in the predetermined direction. Otherwise, the direction of polarization of the light beams 13 may be controlled by a wavelength plate.

In this particular embodiment, the light beams 13 impinge upon in parallel the two interfaces 50f and 50g of the measuring portion 63 of each flow passage 60 of the measuring unit 10 as shown in FIG. 7. Nothing is fixed to the metal film 55 on the interface 50f whereas a sensing material 73 is fixed to the metal film 55 on the interface 50g. The sensing material 73 will be described later.

Analysis of the sample by the surface plasmon resonance sensor will be described, hereinbelow. Prior to measurement, the measuring unit 10 is moved to a measuring position on a chip holding portion 11 from an incubator 2. In the chip holding portion 11, a rail 11a to be engaged with the sliding groove 50e of the dielectric block 50 so that high positional accuracy can be ensured when the measuring unit 10 is moved. After being placed on the chip holding portion 11, the perpendicular projections 50d on the dielectric block 50 is sandwiched by a fixing mechanism (not shown), whereby the measuring unit 10 is fixed in the measuring position on the chip holding portion 11. Thereafter, as shown in FIG. 7, a pipette chip 70 for supplying a liquid sample is inserted into the inlet 61 of the flow passage member 51 and a pipette chip 71 for sucking a liquid sample is inserted into the outlet 65 of the same, thereby supplying a liquid sample 72 is supplied to the measuring portion 63 of the flow passage 60 from the pipette chip 70 for supplying a liquid sample. Then, the measurement is started.

As shown in FIG. 8, a light beam 13 emitted from the laser 14 as a divergent light beam is converged on the interfaces 50f and 50g between the metal film 55 and the dielectric block 50 by virtue of the optical system 15. Each of the light beams 13 include components impinging upon the interfaces 50f and 50g at various angles of incidence θ. The angles of incidence θ are all not smaller than the angle of total internal reflection. Accordingly, the light beams 13 are reflected in total internal reflection at the interfaces 50f and 50g and the reflected light beams 13 include components reflected at the interfaces 50f and 50g at various angles of reflection.

The two light beams 13 respectively collimated by collimator lenses 16 into parallel light beams after reflected in total internal reflection at the interfaces 50f and 50g are respectively detected by the pair of photodiode arrays 17. In this particular embodiment, each photodiode array 17 comprises a plurality of photodiodes 17a, 17b, 17c . . . which are arranged in a row in a direction substantially perpendicular to the direction, in a plane shown in FIG. 8, in which the collimated light beam 13 travels. That is, each components of the light beams 13 respectively reflected in total internal reflection at the interfaces 50*f* and 50*g* at various reflecting angles are received by different photodiodes.

FIG. 9 is a block diagram showing an electric arrangement of the surface plasmon resonance sensor. As shown in FIG. 9, the driver 19 comprises sample hold circuits 22*a*, 22*b*, 22*c* . . . which hold the outputs of respective differential amplifiers 18*a*, 18*b*, 18*c* . . . of the differential amplifier array 18, a multiplexer 23 into which outputs of the sample hold circuits 22*a*, 22*b*, 22*c* . . . are input, an A/D converter 24 which digitizes the output of the multiplexer 23 and inputs the digitized output of the multiplexer 23 into the signal processing portion 20, a driving circuit 25 which drives the multiplexer 23 and the sample hold circuits 22*a*, 22*b*, 22*c* . . . , and a controller 26 which controls the driving circuit 25 under an instruction from the signal processing portion 20. The differential amplifier array 18, the driver 19 and the signal processing portion 20 execute the similar processes to the inputs from the pair of photodiode arrays 17.

Each of the outputs of the photodiodes 17*a*, 17*b*, 17*c* . . . is input into one of the differential amplifiers 18*a*, 18*b*, 18*c* . . . . At this time, outputs of adjacent two photodiodes are into one differential amplifier. Accordingly, the outputs of the respective differential amplifiers 18*a*, 18*b*, 18*c* . . . may be considered to be differentials of the light detecting signals output from the photodiodes 17*a*, 17*b*, 17*c* . . . in the direction in which the photodiodes 17*a*, 17*b*, 17*c* . . . are arranged.

The outputs of the differential amplifiers 18*a*, 18*b*, 18*c* . . . are held by the sample hold circuits 22*a*, 22*b*, 22*c* . . . at a predetermined timing and input into the multiplexer 23. The multiplexer 23 inputs the outputs of the differential amplifiers 18*a*, 18*b*, 18*c* . . . held by the sample hold circuits 22*a*, 22*b*, 22*c* . . . into the A/D converter 24 in a predetermined order. The A/D converter 24 digitizes the outputs and inputs the digitized outputs into the signal processing portion 20.

FIGS. 10A, 10B and 10C are views for illustrating the intensity of the light beam 13 reflected in total internal reflection at the interface 50*f* (or 50*g*) for each angle of incidence θ. The relation between the angle of incidence θ of the light beam 13 to the interface 50*f* (or 50*g*) and intensity I is as shown by the graph shown in FIG. 10A.

The component impinging upon the interface 50*f* (or 50*g*) at a particular angle of incidence θsp excites the surface plasmon at the interface between the metal film 55 and the liquid sample 72 and the intensity I of light reflected in total internal reflection sharply drops for this component. That is, the angle of incidence θsp is the attenuation angle and the intensity I is minimized at the angle θsp. The drop of the intensity I is observed as a dark line in the reflected light beams as denoted by D in FIG. 8.

FIG. 10B shows the direction in which the photodiodes 17*a*, 17*b*, 17*c* . . . are arranged. As described above, the positions of the photodiodes 17*a*, 17*b*, 17*c* . . . correspond to the angles of incidence θ in the direction in which the photodiodes 17*a*, 17*b*, 17*c* . . . are arranged.

The relation between the positions of the photodiodes 17*a*, 17*b*, 17*c* . . . in the direction in which the photodiodes 17*a*, 17*b*, 17*c* . . . are arranged, that is, the angles of incidence θ and the outputs I' of the differential amplifiers 18*a*, 18*b*, 18*c* . . . (differentials of the intensity I) is as shown on FIG. 10C.

The signal processing portion 20 selects a differential amplifier out of the differential amplifiers 18*a*, 18*b*, 18*c* . . . whose output is the closest to the differential I' for the attenuation angle θsp (I'=0) on the basis of the differentials I' input from the A/D converter 24 (amplifier 18*d* in this particular example), and causes the display portion 21 to display the value after a predetermined correction. When there is a differential amplifier which outputs 0 (differential I'=0), it is needless to say that the signal processing portion 20 selects the differential amplifier in such a case.

Thereafter, each time a predetermined time lapses, the differential I' output from the selected differential amplifier 18*d* is displayed by the display portion 21 after the predetermined correction. The differential I' becomes larger or smaller as the dielectric constant or the refractive index of the material in contact with the film 55 of the measuring chip changes and the attenuation angle θsp changes so that the curve shown in FIG. 10A moves left and right. Accordingly, by measuring the differential I' continuously with lapse of time, the change of the refractive index of the liquid sample 72 (or the sensing material 73) in contact with the metal film 55 can be detected.

Especially, in this embodiment, since the refractive index of the sensing material 73 changes with combination of the sensing material 73 and the sample when the sample is the specific material which is combined with the sensing material 73, whether the sample is the specific material which is combined with the sensing material 73 can be detected by continuously measuring the differential I'.

Further, in this particular embodiment, since the metal film 55 has an area where the sensing material 73 is not fixed and an area where the sensing material 73 is fixed so that a reference measurement and a measurement of combination of the sensing material 73 and a sample are simultaneously effected, measuring errors due to, for instance, the change of the temperature of the liquid sample can be cancelled by obtaining the difference between the values detected on the two areas.

Though, in this embodiment, the metal film 55 is used as the measuring surface for the reference measurement, it is preferred that the measuring surface for the reference measurement does not react the object to be measured in the liquid sample 72. For this purpose, the measuring surface for the reference measurement may be, for instance, alkylthiol, aminoalcohol, or aminoether while the measuring surface for the measurement of combination of the sensing material 73 and a sample comprises an antibody as the sensing material.

The use of this embodiment need not be limited to simultaneously effect a reference measurement and a measurement of combination of the sensing material 73 and a sample but embodiments where a measuring surface formed by another flow passage is used in the reference measurement or the reference measurement is not effected may be possible.

Further, the measuring system need not be limited to those where the measurements on all the flow passages formed by the measuring unit are simultaneously effected by a plurality of surface plasmon measuring systems but may be provided with a single surface plasmon measuring system so that a plurality of flow passages formed by a measuring unit are measured in sequence by moving the measuring unit relatively to the measuring system.

A measuring unit in accordance with a second embodiment of the present invention will be described with reference to FIG. 11, hereinbelow. In FIG. 11, elements analogous to those shown in FIG. 8 are given the same reference numerals and will not be described here unless necessary. The measuring unit of the second embodiment is used for a leaky mode sensor and the same in the measuring system as the surface plasmon resonance sensor of the first embodiment.

This measuring unit 10' comprises a clad layer 56 and a waveguide layer 57 which are formed on one surface (an upper surface in the illustrated embodiment) of the dielectric block 50. The dielectric block 50 is formed by synthetic resin, optical glass of BK7, or the like. The clad layer 56 is formed into film by a dielectric material or a metal such as gold which is lower in refractive index than the dielectric block 50 and the waveguide layer 57 is formed into film by a dielectric material such as PMMA which is higher in refractive index than the clad layer 56. The clad layer 56 is 36.5 nm in thickness when formed by metal film, and the waveguide layer 57 is 700 nm in thickness when formed by PMMA.

In the leaky mode sensor with this arrangement, when the light beam 13 emitted from the laser 14 is split into a pair of light beams 13 and caused to impinge upon the clad layer 56 through the dielectric block 50 at an angle not smaller than an angle of total internal reflection, the light beam 13 is reflected in total internal reflection at the interface 50f or 50g between the dielectric block 50 and the clad layer 56. However, light having a particular wave number and impinging upon the optical waveguide layer 57 at a particular angle of incidence comes to propagate through the optical waveguide layer 57 in a waveguide mode after passing through the clad layer 56. When the waveguide mode is thus excited, almost all the incident light is taken in the optical waveguide layer and accordingly, the intensity of light reflected in total internal reflection at the interface 50f or 50g sharply drops. That is, attenuation in total internal reflection occurs.

Since the wave number of light to be propagated through the optical waveguide layer 57 in a waveguide mode depends upon the refractive index of the liquid sample 72 or the sensing material 73 on the optical waveguide layer 57, the refractive index of the liquid sample 72 or the sensing material 73 can be detected on the basis of the angle of incidence θsp at which the attenuation in total internal reflection occurs. Change of the combination of the sensing material 73 and the object to be measured in the liquid sample 72 can detected on the basis of the differentials I' output by the respective differential amplifiers of the differential amplifier array 18.

With this embodiment, result similar to that obtained by the first embodiment can be obtained.

A third embodiment of the present invention will be described with reference to FIG. 12, hereinbelow. In FIG. 12, elements analogous to those shown in FIG. 8 are given the same reference numerals and will not be described here unless necessary. The measuring unit of the third embodiment is the same as that of the first embodiment. However, the measuring system of this embodiment is modified from that of the surface plasmon resonance sensor of the first embodiment.

FIG. 12 shows a profile of the surface plasmon resonance sensor of this embodiment. In the measuring position of the surface plasmon resonance sensor of this embodiment, a laser 120 and a CCD 121 are disposed, and a collimator lens 122, an interference optical system 123, a condenser lens 124 and an aperture member 125 are disposed between the laser 120 and the CCD 121. These are provided in pairs so that the interfaces 50f and 50g of the measuring unit 10 can be measured in parallel.

The interference optical system 123 comprises a polarizing filter 131, a half-silvered mirrors 132 and 133, and a mirror 134. The CCD 121 is connected to a measuring means 135 and the measuring means 135 is connected to the display portion 21.

Measurement in the surface plasmon resonance sensor of this embodiment will be described, hereinbelow. The laser 120 is driven to emit a light beam 140 as a divergent light. The light beam 140 is collimated by the collimator lenses 122 into a parallel light beam and then impinges upon the polarizing filter 131. The light beam 140 passing through the polarizing filter 131 and caused to impinge upon the interface 50f or 50g in the form of p-polarized light is partly split by the half-silvered mirror 132 as a reference light beam 140R, while the other of the light beam 140 passes through the half-silvered mirror 132 and impinges upon the interface 50f or 50g. The other light beam 140S passing through the half-silvered mirror 132 and impinging upon the interface 50f or 50g is reflected in total internal reflection at the interface 50f or 50g and the light beam 140S reflected in total internal reflection at the interface 50f or 50g and the reference light beam 140R reflected by the mirror 134 impinge upon the half-silvered mirror 133 to be synthesized. The synthesized light beam 140' is collected by the condenser lens 124 and then detected by the CCD 121 through the aperture member 125. The light beam 140' detected by the CCD 121 at this time generates interference fringes according to the interference between the light beam 140S and the reference light beam 140R.

Whether the sample in the liquid sample 72 is combined with the sensing material 73 fixed to the surface of the metal film 55 can be determined by detecting the change of the interference fringes detected by the CCD 121 by continuous measurements after supply of a liquid sample 72 into the flow passage 60.

That is, since the refractive index of the sensing material 73 changes with the state of combination of the object to be measured in the liquid sample 72 with the sensing material 73, the state of interference changes when the light beam 140S reflected in total internal reflection at the interface 50f or 50g is synthesized with the reference light beam 140R. Accordingly, whether there is a combining reaction can be detected according to the change of the interference fringes. On the basis of the above principle, the measuring means 135 detects whether there is a combining reaction, and the display portion 21 displays the result of the detection.

With this embodiment, result similar to that obtained by the first embodiment can be obtained.

Though, in the first to third embodiments described above, a plurality of flow passages 60 are linearly arranged, the flow passage may be single or a plurality of flow passages 60 may be arranged like a matrix.

A slit portion 51b or a septum portion 51c may be formed at the inlet portion 61 and the outlet portion 65 of the flow passage 60 formed by the flow passage member 51' as shown in FIGS. 13A and 13B or 14A and 14B. By this, evaporation of the liquid sample can be prevented and change of the refractive index of the sample due to evaporation of the liquid sample can be prevented, whereby the measuring signal can be stabilized.

It is possible to arrange the measuring unit of the present invention so that a semi-cylindrical prism 81 which causes the light beam emitted from the light source of the measuring system to impinge upon the interface between the dielectric block 50' and the metal film 55 and causes the light beam reflected in total internal reflection at the interface to emit toward the photodetector means of the measuring system is formed separately from the dielectric block 50' as shown in FIG. 15. In this case, the dielectric block 50' and the prism 81 is bonded by way of a matching oil 80. The shape of the prism 81 need not be limited to that described above, but may be various including a triangle or a rectangle (in cross section) according to the optical system of the measuring system.

What is claimed is:

1. A measuring unit comprising
a dielectric block which is transparent to a light beam and has a flat and smooth surface on which a film layer is formed, and
a flow passage member held in close contact with the film layer,
wherein the flow passage member is provided with a passage comprising a supply passage extending from an inlet of the flow passage member to a measuring portion and a discharge passage extending from the measuring portion to an outlet of the flow passage member,
wherein the flow passage member is formed by an elastic material, and
wherein the flow passage member is provided with a slit portion or a septum portion at its inlet portion and/or outlet portion.

2. The measuring unit as defined in claim 1, wherein the flow passage member comprises:
a plurality of supply passages;
a plurality of inlets; and
a plurality of outlets,
wherein each one of the plurality of supply passages respectively extend between one of the plurality of inlets and one of the plurality of outlets.

3. The measuring unit as defined in claim 1, wherein the flow passage member comprises:
an upper portion; and
a seal portion, the seal portion integrally formed with the upper portion,
wherein the seal portion is held in close contact with the film layer.

4. The measuring unit as defined in claim 3, wherein the seal portion is an O-ring.

5. The measuring unit as defined in claim 3, wherein the flow passage member is provided with at least one of a plurality of slit portions and a plurality of septum portions.

6. A measuring unit comprising
a dielectric block which is transparent to a light beam and has a flat and smooth surface on which a film layer is formed,
a flow passage member held in close contact with the film layer, and
a holding member which is engaged with the dielectric block to hold the flow passage member on one surface of the dielectric block,
wherein the flow passage member is provided with a passage comprising a supply passage extending from an inlet of the flow passage member to a measuring portion and a discharge passage extending from the measuring portion to an outlet of the flow passage member.

7. A measuring unit as defined in claim 6 in which the holding member is provided with a holding plate portion which is held in close contact with the surface of the flow passage member in which each of the inlet and the outlet is formed, and
the holding plate portion is provided with a tapered insertion hole tapered toward the flow passage member in a position opposed to the inlet or the outlet of the flow passage member.

8. A measuring unit as defined in claim 6, further comprising an evaporation preventing member which seals the inlet and/or the outlet of the flow passage member and prevents a sample from evaporating.

9. A measuring unit as defined in claim 8 in which the holding member and the evaporation preventing member are formed integrally with each other.

10. A measuring unit as defined in claim 8 in which the holding member and the evaporation preventing member are formed separately from each other and are bonded together by an adhesive.

11. A measuring unit as defined in claim 6, further comprising a first pipet chip which supplies a sample to the supply passage and a second pipet chip which sucks a sample from the discharge passage.

12. A measuring unit as defined in claim 6 in which the flow passage member is provided with a slit portion or a septum portion at its inlet portion and/or outlet portion.

13. A measuring unit comprising
a dielectric block which is transparent to a light beam and has a flat and smooth surface on which a film layer is formed,
a flow passage member held in close contact with the film layer, and
an evaporation preventing member which seals the inlet and/or the outlet of the flow passage member and prevents a sample from evaporating,
wherein the flow passage member is provided with a passage comprising a supply passage extending from an inlet of the flow passage member to a measuring portion and a discharge passage extending from the measuring portion to an outlet of the flow passage member.

14. A measuring unit as defined in claim 13 in which the evaporation preventing member is formed by an elastic material and formed with a slit in a position opposed to the inlet and/or the outlet of the flow passage member.

* * * * *